(12) United States Patent
Hanes et al.

(10) Patent No.: US 10,596,170 B2
(45) Date of Patent: *Mar. 24, 2020

(54) TREATMENT OF VASOMOTOR SYMPTOMS

(71) Applicant: Sprout Pharmaceuticals, Inc., Raleigh, NC (US)

(72) Inventors: Vladimir Hanes, Thousand Oaks, CA (US); Anna Elisabeth Verbeek, Sandy Hook, CT (US)

(73) Assignee: Sprout Pharmaceuticals, Inc., Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/200,004

(22) Filed: Nov. 26, 2018

(65) Prior Publication Data

US 2019/0091219 A1 Mar. 28, 2019

Related U.S. Application Data

(63) Continuation of application No. 14/583,275, filed on Dec. 26, 2014, now Pat. No. 10,166,230, which is a continuation of application No. 13/847,683, filed on Mar. 20, 2013, now abandoned, which is a continuation of application No. 12/675,231, filed as application No. PCT/EP2008/062011 on Sep. 11, 2008, now abandoned.

(60) Provisional application No. 60/971,605, filed on Sep. 12, 2007.

(51) Int. Cl.
*A61K 31/496* (2006.01)
*A61P 15/12* (2006.01)

(52) U.S. Cl.
CPC ............ *A61K 31/496* (2013.01); *A61P 15/12* (2018.01)

(58) Field of Classification Search
CPC .............................. A61K 31/496; A61P 15/12
See application file for complete search history.

(56) References Cited

U.S. PATENT DOCUMENTS

| 9,949,969 B2 * | 4/2018 | Hanes | ...................... A61P 15/12 |
| 10,166,230 B2 * | 1/2019 | Hanes | ...................... A61P 15/12 |

* cited by examiner

*Primary Examiner* — Theodore R. West
(74) *Attorney, Agent, or Firm* — Womble Bond Dickinson (US) LLP

(57) ABSTRACT

The invention relates to a method for the treatment of vasomotor symptoms comprising the administration of a therapeutically effective amount of flibanserin.

18 Claims, No Drawings

TREATMENT OF VASOMOTOR SYMPTOMS

RELATED APPLICATIONS

This application is a continuation of U.S. patent application Ser. No. 14/583,275 for Treatment of Vasomotor Symptoms, filed Dec. 26, 2014, which is a continuation of U.S. patent application Ser. No. 13/847,683 for Treatment of Vasomotor Symptoms, filed Mar. 20, 2013, which is a continuation of U.S. patent application Ser. No. 12/675,231 for Treatment of Vasomotor Symptoms, filed Jan. 28, 2011, which claims the benefit of (i) International Application No. PCT/EP2008/062011 for Treatment of Vasomotor Symptoms, filed Sep. 11, 2008, (ii) U.S. Patent Application No. 60/971,605 for Treatment of Vasomotor Symptoms, filed Sep. 12, 2007, each of which is hereby incorporated by reference in its entirety.

The present invention relates to methods for the treatment of vasomotor symptoms associated with the menopause comprising the administration of a therapeutically effective amount of flibanserin.

DESCRIPTION OF THE INVENTION

The compound 1-[2-(4-(3-trifluoromethyl-phenyl)piperazin-1-yl)ethyl]-2,3-dihydro-1H-benzimidazol-2-one (flibanserin) is disclosed in form of its hydrochloride in European Patent Application EP-A-526434 and has the following chemical structure:

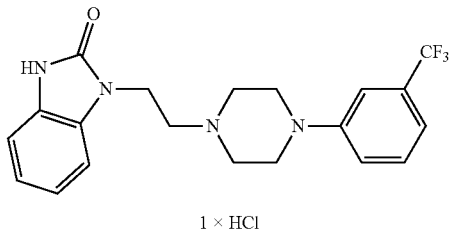

1 × HCl

Flibanserin shows affinity for the $5\text{-HT}_{1A}$ and $5\text{-HT}_2$-receptor. It is therefore a promising therapeutic agent for the treatment of a variety of diseases, for instance depression, schizophrenia, and anxiety.

Women transitioning through the menopausal frequently experience a variety of symptoms which have been attributed to estrogen deprivation due to ovarian failure. Menopause is defined as the cessation of menstruation in women. The timing of the menopause is determenied with hind sight and is established after twelve months of amenorrhoea. Most women experience menopause between the ages of 40 and 55. Menopausal transition is characterized by hot flashes, headaches, night sweats, atrophic vaginitis, frequent urinary tract infections, cold hands and feet, forgetfulness and an inability to concentrate. Emotional indicators of menopause transitioning include anxiety, distress, irritability, mood swings, depression and decreased sex drive. There are many undesirable symptoms too numerous to articulate which are attributed to changes in the female body as she transitions through the menopause.

Some of the symptoms, e.g., vulvar and vaginal atrophy can be clearly attributed to estrogen deficiency; however, hot flashes are likely to arise as a result of an alteration in the CNS thermoregulatory set-point located in the anterior portion of the hypothalamus. Hot flashes, also known as "vasomotor flushes" or "hot flushes" are very common in peri- and postmenopausal women. The dilation of peripheral blood vessels results in reddening and warming of the skin during a hot flash. Further symptoms such as increased heart rate, night sweats, headaches, dizziness, weight gain, fatigue and insomnia may be associated with a hot flash. Hot flashes may appear prior to the cessation of the menses and may be the first sign that menopause is approaching. During the perimenopausal period, appr. 75% of women complain of hot flashes. In most of these women the symptoms will last appr. 1 year. About one-third of postmenopausal women will report symptoms that last up to 5 years after natural menopause, and hot flashes can persist for up to 15 years in 20% or more of women. Menopause induced by surgery is associated with about a 90% probability of hot flashes during the first year, and hot flashes associated with surgical menopause are often more abrupt and severe and can last longer than those associated with a non-surgical menopause.

The US Bureau of Census estimates that currently 49 million American women are over the age of 50 years. Thus, over 32 million women in the USA today might have had hot flashes, and up to 6 million might have reported severe symptoms.

Now, experimental results from studies performed in patients with major Depressive Disorder have shown that flibanserin may be useful for the treatment of vasomotor symptoms (e,g, hot flashes, night sweats, moodswings and irritability).

Accordingly, the instant invention relates to a method for the treatment of vasomotor symptoms comprising the administration of a therapeutically effective amount of flibanserin, optionally in form of the free base, the pharmacologically acceptable acid addition salts and/or optionally in form of the hydrates and/or solvates thereof.

In an further aspect, the instant invention relates to a method for the treatment of vasomotor symptoms associated with the menopausal transition comprising the administration of a therapeutically effective amount of flibanserin, optionally in form of the free base, the pharmacologically acceptable acid addition salts and/or optionally in form of the hydrates and/or solvates thereof.

As vasomotors symptoms do not only occur due to naturally occurring menopause but may also be also due to surgically (e.g., hysterectomy and bilateral ovarectomy) induced menopause or by the use of medications (e.g. by selective estrogen receptor modulators, GnRH analogues and Aromatase inhibitors), or induced by radioation and chemotherapeutic agents, the present invention relates to a method for the treatment or prevention of vasomotor symptoms associated with iatrogenic induced menopause, comprising the administration of a therapeutically effective amount of flibanserin, optionally in form of the free base, the pharmacologically acceptable acid addition salts and/or optionally in form of the hydrates and/or solvates thereof.

In another embodiment the present invention refers to a method for the treatment of hot flashes, night sweats, moodswings and irritability comprising the administration of a therapeutically effective amount of flibanserin, optionally in form of the free base, the pharmacologically acceptable acid addition salts and/or optionally in form of the hydrates and/or solvates thereof.

Another aspect of the present invention relates to the use of flibanserin for the treatment of moderate to severe vasomotor symptoms associated with a natural or iatrogenic hypogonadal state in men.

Still further aspect of the present invention relates to use of flibanserin for treatment of hot flushes in men, preferably in hypogonadal men, men on androgen deprivation treatment or those who underwent castration.

Another embodiment of the invention relates to the use of flibanserin, optionally in form of the free base, the pharmacologically acceptable acid addition salts and/or optionally in form of the hydrates and/or solvates thereof for the preparation of a medicament for the treatment of any one of the above mentioned conditions. As already mentioned above, Flibanserin may be used in form of the free base, optionally in form of its pharmaceutically acceptable acid addition salts and/or optionally in form of the hydrates and/or solvates thereof. Suitable acid addition salts include for example those of the acids selected from, succinic acid, hydrobromic acid, acetic acid, fumaric acid, maleic acid, methanesulphonic acid, lactic acid, phosphoric acid, hydrochloric acid, sulphuric acid, tartaric acid and citric acid. Mixtures of the abovementioned acid addition salts may also be used. From the aforementioned acid addition salts the hydrochloride and the hydrobromide, particularly the hydrochloride, are preferred. If Flibanserin is used in form of the free base, it is preferably used in form of Flibanserin polymorph A as disclosed in WO 03/014079.

Flibanserin, optionally in form of the free base, the pharmacologically acceptable acid addition salts and/or optionally in form of the hydrates and/or solvates, may be incorporated into the conventional pharmaceutical preparation in solid, liquid or spray form. The composition may, for example, be presented in a form suitable for oral, rectal, parenteral administration or for nasal inhalation: preferred forms includes for example, capsules, tablets, coated tablets, ampoules, suppositories and nasal spray.

The active ingredient may be incorporated in excipients or carriers conventionally used in pharmaceutical compositions such as, for example, talc, arabic gum, lactose, gelatine, magnesium stearate, corn starch, acqueous or non acqueous vehicles, polyvynil pyrrolidone, semisynthetic gliderides of fatty acids, benzalconium chloride, sodium phosphate, EDTA, polysorbate 80. The compositions are advantageously formulated in dosage units, each dosage unit being adapted to supply a single dose of the active ingredient. The dosis range applicable per day is between 0.1 to 400, preferably between 1.0 to 300, more preferably between 2 to 200 mg.

Each dosage unit may conveniently contain from 0.01 mg to 100 mg, preferably from 0.1 to 50 mg.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g of. a flavouring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g of. with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

The Examples which follow illustrate the present invention without restricting its scope:

EXAMPLES

Clinical Trial

In twelve Phase II clinical studies performed in patients diagnosed with Major Depressive Disorder, more then 1500 male and female subjects aged between 18 and 65 years received one or more doses of flibanserin ranging from 2 mg to 100 mg b.i.d. A preliminary analysis of safety database in these subjects showed that flibanserin was associated with virtually no AEs coded as hot flushes/flushing as compared to placebo (1.25%) or selective serotonin reuptake inhibitors (2.1%). (see table 1).

TABLE 1

|  | | Flibanserin in mg | | | | | | Paroxetine in mg | Fluoxetine in mg |
| --- | --- | --- | --- | --- | --- | --- | --- | --- | --- |
| Treatment | Placebo | 20 bid | 50 bid | 100 bid | 20 qd | 50 qd | 100 qd | 2 bid | 20 | 20 |
| N | 718 | 225 | 521 | 154 | 63 | 64 | 63 | 120 | 275 | 145 |
| flushing | 5 | 2 | 0 | 0 | 1 | 0 | 0 | 1 | 2 | 2 |
| Hot flush | 4 | 2 | 1 | 0 | 0 | 0 | 0 | 1 | 3 | 2 |

In Table 1 it is shown that 9 patients of 718 receiving placebo (1.25%), 5 patients of 275 (1.8%) or 4 of 145 (2.75%) receiving Paroxetine or Fluoxetine respectively suffered form flushing or hot flushes. In stark contrast, in the group receiving 50 to 200 mg/day Flibanserin only one out of 802 patients suffered from flushing. These data suggest that flibanserin is useful for the treatment of vasomotor symptoms like hot flushes in menopausal women.

Examples of Pharmaceutical Formulations

A)

| Tablets | per tablet |
|---|---|
| flibanserin hydrochloride | 100 mg |
| lactose | 240 mg |
| corn starch | 340 mg |
| polyvinylpyrrolidone | 45 mg |
| magnesium stearate | 15 mg |
| | 740 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B)

| Tablets | per tablet |
|---|---|
| flibanserin hydrochloride | 80 mg |
| corn starch | 190 mg |
| lactose | 55 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

C)

| Coated tablets | per coated tablet |
|---|---|
| flibanserin hydrochloride | 5 mg |
| corn starch | 41.5 mg |
| lactose | 30 mg |
| polyvinylpyrrolidone | 3 mg |
| magnesium stearate | 0.5 mg |
| | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

D)

| Capsules | per capsule |
|---|---|
| flibanserin hydrochloride | 150 mg |
| Corn starch | 268.5 mg |
| Magnesium stearate | 1.5 mg |
| | 420 mg |

The substance and corn starch are mixed and moistened with water. The moist mass is screened and dried. The dry granules are screened and mixed with magnesium stearate. The finished mixture is packed into size 1 hard gelatine capsules.

E)

| Ampoule solution | |
|---|---|
| flibanserin hydrochloride | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion.

F) Suppositories

| flibanserin hydrochloride | 50 mg |
|---|---|
| solid fat | 1650 mg |
| | 1700 mg |

The hard fat is melted. At 40° C. the ground active substance is homogeneously dispersed. It is cooled to 38° C. and poured into slightly chilled suppository moulds.

In a particular preferred embodiment of the instant invention, flibanserin is administered in form of specific film coated tablets. Examples of these preferred formulations are listed below. The film coated tablets listed below can be manufactured according to procedures known in the art (see hereto WO 03/097058).

G) Film Coated Tablet
Core

| Constituents | mg/tablet |
|---|---|
| Flibanserin | 25.000 |
| Lactose monohydrate | 71.720 |
| Microcrystalline cellulose | 23.905 |
| HPMC (Methocel E5) | 1.250 |
| Carboxymethylcellulose sodium | 2.500 |
| Magnesium stearate | 0.625 |

Coating

| Constituents | mg/tablet |
|---|---|
| HPMC (Methocel E5) | 1.440 |
| Polyethylene Glycol 6000 | 0.420 |
| Titanium dioxide | 0.600 |
| Talc | 0.514 |

H) Film Coated Tablet
Core

| Constituents | mg/tablet |
| --- | --- |
| Flibanserin | 50.000 |
| Lactose monohydrate | 143.440 |
| Microcrystalline cellulose | 47.810 |
| HPMC (e.g. Pharmacoat 606) | 2.500 |
| Carboxymethylcellulose sodium | 5.000 |
| Magnesium stearate | 1.250 |

Coating

| Constituents | mg/tablet |
| --- | --- |
| HPMC (e.g. Pharmacoat 606) | 2.400 |
| Polyethylene Glycol 6000 | 0.700 |
| Titanium dioxide | 1.000 |
| Talc | 0.857 |
| Iron oxide red | 0.043 |
| Total Film coated tablet | 255.000 |

I) Film Coated Tablet
Core

| Constituents | mg/tablet |
| --- | --- |
| Flibanserin | 100.000 |
| Lactose monohydrate | 171.080 |
| Microcrystalline cellulose | 57.020 |
| HPMC (e.g. Methocel E5) | 3.400 |
| Carboxymethylcellulose sodium | 6.800 |
| Magnesium stearate | 1.700 |

Coating

| Constituents | mg/tablet |
| --- | --- |
| HPMC (e.g. Methocel E5) | 3.360 |
| Polyethylene Glycol 6000 | 0.980 |
| Titanium dioxide | 1.400 |
| Talc | 1.200 |
| Iron oxide red | 0.060 |
| Total Film coated tablet | 347.000 |

J) Film Coated Tablet
Core

| Constituents | mg/tablet |
| --- | --- |
| Flibanserin | 2.000 |
| Dibasic Calciumphosphate, anhydrous | 61.010 |
| Microcrystalline cellulose | 61.010 |
| HPMC (Methocel E5) | 1.950 |
| Carboxymethylcellulose sodium | 2.600 |
| Colloidal silicon dioxide | 0.650 |
| Magnesium stearate | 0.780 |
| Iron oxide red | 0.026 |
| Total Film coated tablet | 128.000 |

Coating

| Constituents | mg/tablet |
| --- | --- |
| HPMC (Methocel E5) | 1.440 |
| Polyethylene Glycol 6000 | 0.420 |
| Titanium dioxide | 0.600 |
| Talc | 0.514 |
| Iron oxide red | 0.026 |
| Total Film coated tablet | 133.000 |

K) Film Coated Tablet
Core

| Constituents | mg/tablet |
| --- | --- |
| Flibanserin | 100.000 |
| Dibasic Calciumphosphate, anhydrous | 69.750 |
| Microcrystalline cellulose | 69.750 |
| HPMC (e.g. Methocel E5) | 2.750 |
| Carboxymethylcellulose sodium | 5.000 |
| Colloidal silicon dioxide | 1.250 |
| Magnesium stearate | 1.500 |

Coating

| Constituents | mg/tablet |
| --- | --- |
| HPMC (e.g. Methocel E5) | 2.400 |
| Polyethylene Glycol 6000 | 0.700 |
| Titanium dioxide | 1.043 |
| Talc | 0.857 |
| Total Film coated tablet | 255.000 |

L) Film Coated Tablet
Core

| Constituents | mg/tablet |
| --- | --- |
| Flibanserin | 20.000 |
| Lactose monohydrate | 130.000 |
| Microcrystalline cellulose | 43.100 |
| Hydroxypropyl Cellulose (e.g. Klucel LF) | 1.900 |
| Sodium Starch Glycolate | 4.000 |
| Magnesium stearate | 1.000 |

Coating

| Constituents | mg/tablet |
| --- | --- |
| HPMC (e.g. Methocel E5) | 2.400 |
| Polyethylene Glycol 6000 | 0.700 |
| Titanium dioxide | 1.043 |
| Talc | 0.857 |
| Total Film coated tablet | 205.000 |

The invention claimed is:

1. A method for the treatment of vasomotor symptoms associated with menopause comprising the oral administration to an adult human patient in need of such treatment of one or more capsule or tablet comprising a therapeutically effective amount of flibanserin, or a pharmacologically acceptable acid addition salt, hydrate or solvate, thereof, and at least one excipient, wherein said vasomotor symptoms are selected from the group consisting of hot flashes, hot flushes, night sweats, mood swings, and irritability.

2. The method according to claim 1, wherein the vasomotor symptoms are hot flashes or hot flushes.

3. The method according to claim 1, wherein the vasomotor symptoms are night sweats.

4. The method according to claim 1, wherein the vasomotor symptoms are mood swings.

5. The method according to claim 1, wherein the vasomotor symptoms are irritability.

6. The method according to claim 1, wherein menopause is naturally occurring.

7. The method according to claim 1, wherein menopause is surgically induced.

8. The method according to claim 1, wherein menopause is iatrogenic induced.

9. The method according to claim 1, wherein menopause is associated with the use of medication, radiation, or chemotherapeutic agents.

10. The method according to claim 1, wherein the flibanserin is administered as a pharmaceutically acceptable acid addition salt selected from the salts formed by succinic acid, hydrobromic acid, acetic acid, fumaric acid, maleic acid, methanesulphonic acid, lactic acid, phosphoric acid, hydrochloric acid, sulphuric acid, tartaric acid, citric acid, and mixtures thereof.

11. The method according to claim 1, wherein the patient is a menopausal woman.

12. The method according to claim 1, wherein the patient is a postmenopausal woman.

13. The method according to claim 1, wherein the patient is a perimenopausal woman.

14. The method according to claim 1, wherein the amount administered is in one capsule or tablet containing between 0.1 to 400 mg per day of flibanserin.

15. The method according to claim 1, wherein the amount administered is in one capsule or tablet containing between 1.0 and 300 mg per day of flibanserin.

16. The method according to claim 1, wherein the amount administered is in one capsule or tablet containing between 2 and 200 mg per day of flibanserin.

17. The method according to claim 1, wherein the amount administered is in one capsule or tablet containing between 0.01 to 100 mg per day of flibanserin.

18. The method according to claim 1, wherein the amount administered is in one capsule or tablet containing between 0.1 to 50 mg per day of flibanserin.

* * * * *